United States Patent

Palumbo et al.

[11] Patent Number: 5,944,706
[45] Date of Patent: Aug. 31, 1999

[54] LAYERED, ABSORBENT STRUCTURE, AN ABSORBENT ARTICLE COMPRISING THE STRUCTURE, AND A METHOD FOR THE MANUFACTURE THEREOF

[75] Inventors: Gianfranco Palumbo, Pescara; Giovanni Carlucci, Chieti, both of Italy

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/669,451
[22] PCT Filed: Dec. 19, 1994
[86] PCT No.: PCT/EP94/04215
  § 371 Date: Nov. 21, 1996
  § 102(e) Date: Nov. 21, 1996
[87] PCT Pub. No.: WO95/17868
  PCT Pub. Date: Jul. 6, 1995

[30] Foreign Application Priority Data

Dec. 31, 1993 [IT] Italy .................................. T093A1028

[51] Int. Cl.⁶ .............................. A61F 13/15; A61F 13/20
[52] U.S. Cl. ............................................ 604/368; 604/378
[58] Field of Search .................................... 604/378, 358, 604/365–368, 370

[56] References Cited

U.S. PATENT DOCUMENTS

| 4,857,065 | 8/1989 | Seal | 604/368 |
|---|---|---|---|
| 5,175,046 | 12/1992 | Nguyen | 428/198 |
| 5,352,480 | 10/1994 | Hansen et al. | 604/368 |
| 5,360,420 | 11/1994 | Cook et al. | 604/368 |
| 5,387,208 | 2/1995 | Ashton et al. | 604/368 |
| 5,589,256 | 12/1996 | Hansen t al. | 604/378 |
| 5,599,335 | 2/1997 | Goldman et al. | 604/368 |
| 5,607,414 | 3/1997 | Richards et al. | 604/368 |
| 5,653,702 | 8/1997 | Brohammer et al. | 604/378 |

FOREIGN PATENT DOCUMENTS

| 0 321755 | 6/1989 | European Pat. Off. . |
|---|---|---|
| 0 374910 A1 | 6/1990 | European Pat. Off. . |
| 2 252 047 | 7/1992 | United Kingdom . |
| 2 269 109 | 2/1994 | United Kingdom . |
| WO 90/05513 | 5/1990 | WIPO . |
| WO 92/11830 | 7/1992 | WIPO . |
| WO 94/01069 | 1/1994 | WIPO . |
| WO 94/02093 | 2/1994 | WIPO . |

*Primary Examiner*—Mickey Yu
*Assistant Examiner*—Tram A. Nguyen
*Attorney, Agent, or Firm*—Kevin D. Hogg; Carl J. Roof; Steven W. Miller

[57] ABSTRACT

Disclosed is a thin, layered, absorbent structure comprising first and second layers of fibrous material and an intermediate layer comprising particles of a hydrogelling, absorbent material, in an amount exceeding 120 g/m², and particles of a thermoplastic, polymeric, organic material; the first and second fibrous layers extend beyond the intermediate layer laterally to form longitudinal edge portions. The two fibrous layers are bound together with the intermediate layer between them by the melting of the particles of thermoplastic, polymeric, organic material and by means of a continuous line of adhesive extending longitudinally on each longitudinal edge portion.

32 Claims, 2 Drawing Sheets

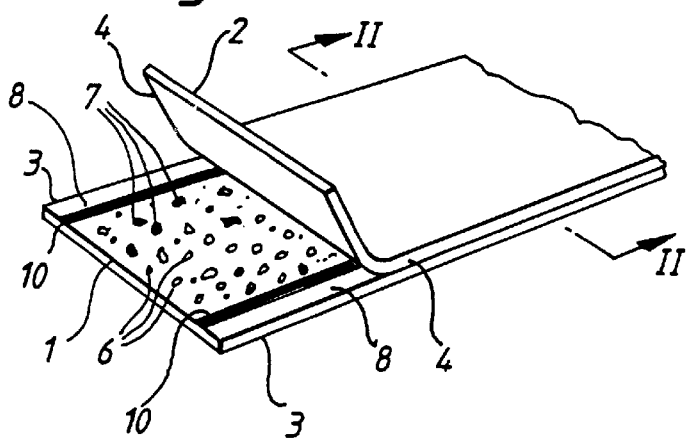
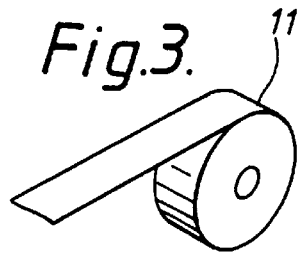
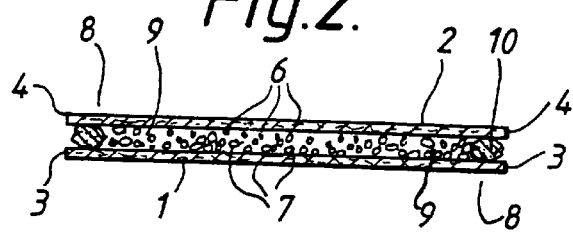
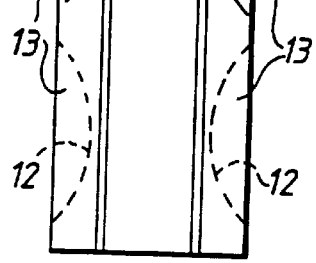
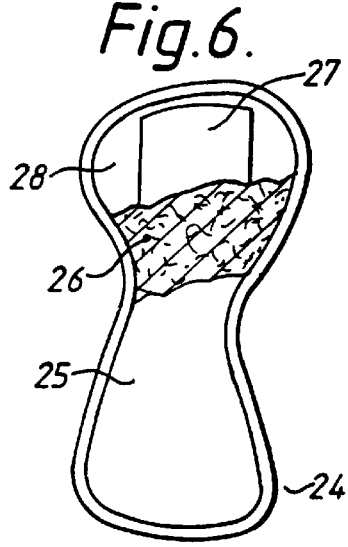
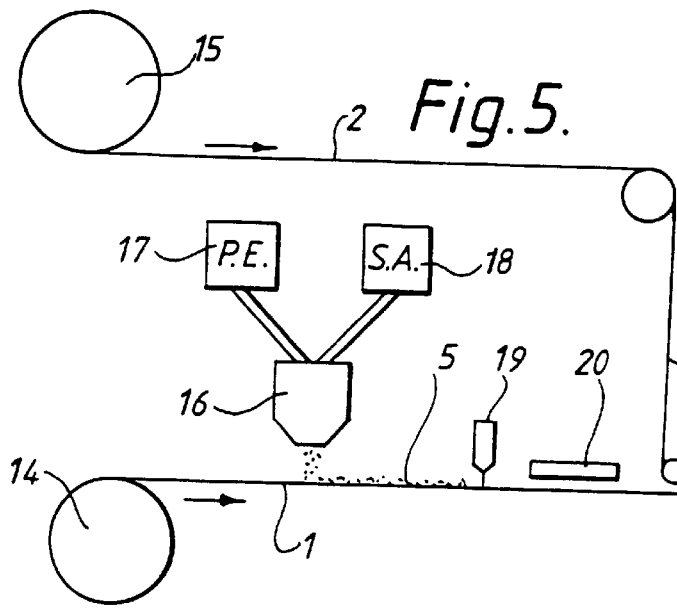

LAYERED, ABSORBENT STRUCTURE, AN ABSORBENT ARTICLE COMPRISING THE STRUCTURE, AND A METHOD FOR THE MANUFACTURE THEREOF

CROSS REFERENCE TO RELATED APPLICATIONS

This application claims priority under 35 USC §371 to International Patent Application No. PCT/EP94/04215, filed Dec. 19, 1994, which claims priority to Italian Patent Application No. TO93A001028, filed Dec. 31, 1993.

BACKGROUND OF THE INVENTION

The present invention relates to layered, absorbent structures constituted by fibrous layers with interposed particles of hydrogelling absorbent material.

The structures may be used as absorbent elements in disposable absorbent articles such as absorbent articles for incontinent adults, babies' nappies, sanitary towels, dressings and the like.

Disposable absorbent articles are well known and all have absorbent elements for absorbing and retailing body fluids; an absorbent element must be able to acquire liquid rapidly and to distribute it internally so as to prevent leakages and must also have a good capacity to retain the fluids when subjected to the normal pressures of use.

Absorbent elements made mainly of hydrophilic fibrous material such as, for example, pads of cellulose fibres, layers of wadding, or the like generally have satisfactory characteristics as regards their liquid-absorption rate and can distribute the liquid effectively within them but are very ineffective from the point of view of retention when subjected to the normal pressures of use.

The use of hydrogelling absorbent materials in combination with hydrophilic fibres in order to increase the absorption and retention capacities of the absorbent elements is known.

Hydrogelling absorbent materials, commonly known as superabsorbents, are polymers which can swell up and absorb large quantities of liquid, particularly water, or also, to a lesser extent, body fluids.

They also have the particular property that they retain the fluids even under moderate pressure; owing to this characteristic, their use in absorbent elements for disposable absorbent articles has been proposed for some time.

The high absorption capacity of superabsorbents is not, however, combined with similarly rapid absorption and this may adversely affect the performance of absorbent articles incorporating these substances.

In fact, superabsorbents may give rise to a phenomenon defined in the prior art as "gel blocking"; when a particle of superabsorbent is in contact with the liquid, its external surface starts to absorb the liquid and swells up obstructing the transmission of the liquid into the particle itself; the liquid can penetrate further into the still-dry core of the particle only by means of a very slow diffusion mechanism.

This phenomenon may prevent full use being made of the large absorption capacities of superabsorbent substances.

Leaving out of consideration the type of superabsorbent material and the shapes and sizes of the particles, "gel blocking" is generally encouraged by the formation of agglomerations of superabsorbent particles within the absorbent structure, which may occur either before use, when the particles are still dry, or during use, when the particles start to absorb the liquid and swell up.

In any case, with the use of hydrogelling absorbent materials, it is possible to produce absorbent elements which contain less hydrophilic fibres for a given absorption capacity and which consequently have smaller dimensions, particularly thicknesses, than conventional absorbent elements made of fibres alone.

Structures have been formed in which the fibres and the particles of hydrogelling, absorbent material are disposed in separate, generally very thin, superposed layers.

Many particular forms of layered, absorbent structures of this type, in which the fibrous material is represented by one or more layers of wadding, absorbent paper or non-woven fabric, and in which the particles of hydrogelling absorbent material are incorporated in the structure in various ways, are known in the art.

In layered structures which are formed dry, the at least two fibrous layers are bound together solely by the intertwining of fibres and the particles of hydrogelling absorbent material between them are held in position by the two fibrous layers joined together; a better connection between the fibrous layers can be achieved by subjecting the structure to an embossing process which encourages the fibres to intertwine by causing slight relative slippage between the layers, as described in U.S. Pat. No. 4,578,068.

Alternatively, the layered structure may be formed damp by the application of water, or preferably steam, and pressure; the connection between the fibrous layers is achieved mainly by virtue of the particles of hydrogelling, absorbent material which become sticky and act as an adhesive between the fibrous layers.

In neither case is the structure very stable and the fibrous layers may separate, for example, along their edges, leaving the particles of hydrogelling absorbent material free to slide between the surfaces of the layers between which they are included; the particles of hydrogelling absorbent material may thus become concentrated locally thereby encouraging, and possibly aggravating, the establishment of the "gel blocking" phenomenon in use, and may also escape from the edges of the structure, in any case reducing the absorption capacity of the structure.

Another solution for the formation of a layered absorbent structure provides for the use of an adhesive, for example, of the hot melting type, applied to the surface of one of the fibrous layers with the dual purpose of bonding the two fibrous layers together and simultaneously fixing the particles of superabsorbent material between them.

The use of an adhesive may, however, affect the absorption characteristics both of the fibrous layer to which the adhesive is applied, and of the superabsorbent particles which come into contact with the adhesive.

In general, therefore, it is necessary not to use an excessive quantity of adhesive and consequently not to eliminate completely the possibility of the loss of superabsorbent material from the edges of the layered structure.

For this reason, layered absorbent structures of the type described are formed directly on the production line for the absorbent articles in which they are to be incorporated, since it is not convenient to produce them independently as semi-finished products.

The problem of the loss of hydrogelling absorbent material along the edges is common to all the layered structures described up to now and has been solved in various ways in known products; for example, by surrounding the structure completely with a layer of wadding, which involves the addition of a further element, or by the use of a single layer of fibrous material on which the adhesive and the superabsorbent material are distributed only on a central longitudinal strip and subsequently folding the two side portions so that they partially overlap approximately on the longitudinal axis.

This solution solves the problem of the loss of hydrogelling absorbent material from the edges of the structure without requiring the presence of additional elements but does not allow different materials to be used for the two fibrous layers. Moreover, it involves the use of a larger quantity of material than would be needed simply to superpose two layers of the same width as the finished product.

There remains therefore the problem of providing a thin, layered, absorbent structure which does not have the disadvantages described above connected with the method of joining together the various layers of which it is made up and, preferably, of reducing the quantity of material so as to produce a thinner and lighter structure.

The invention described in International Patent Application No PCT/US93/06128 filed Jun. 25, 1993 and claiming priority from Italian Patent Application No TO92 A 000566 filed Jul. 3, 1992 has the object of improving the absorbtion and stability characteristics of thin, layered, absorbent structures containing hydrogelling, absorbent material for use in disposable absorbent articles.

According to the said invention this object was achieved by virtue of a thin, layered, absorbent structure having the specific characteristics recited in the associated claims.

A further subject of that invention was a method for the manufacture of such a structure.

In summary, that invention related to a thin, layered, absorbent structure formed by at least two fibrous layers comprising between them a layer of particles of hydrogelling, absorbent material, the two fibrous layers being joined together by particles of thermoplastic, polymeric, organic material distributed and mixed with the hydrogelling, absorbent material, and by two lines of adhesive disposed along the longitudinal edges of the structure.

In application PCT/US93/06128, we stated that the quantity of the hydrogelling absorbent material (hereinafter sometimes referred to by its usual abbreviation "AGM") together with the thermoplastic polymeric organic material may be between 30 g/m$^2$ and 150 g/m$^2$.

We further stated that the quantity of the latter material should be between 5 g/m$^2$ and 30 g/m$^2$.

Given that the quantity of the latter material needs to increase as the quantity of AGM increases, the values given above are to be understood as implying that the maximum quantity of AGM is 120 g/m$^2$.

There was indeed a good reason why such a maximum should exist. Photomicrographic analysis of the structure according to PCT/US93/06128 showed that the two fibrous layers were held together by "bridges" between them, formed by a particle of the thermoplastic material which had fused to both fibrous layers, or a plurality of such particles which had fused to one another and, at the ends of the bridge, to the fibrous layers.

Increasing the quantity of AGM would evidently reduce the probability of such bridges being formed, and a point would be reached (and was reached by the time the quantity of AGM had increased to the upper limit of 120 g/m$^2$) where the bridges were too few in number to provide a stable structure.

SUMMARY OF THE INVENTION

It has now been found, however, that by increasing the amount of heat used to bond the fibrous layers to the AGM/thermoplastic material, it is possible to use a quantity of AGM greater than 120 g/m$^2$.

Indeed, it has been found possible to use AGM in an amount of up to 600 g/m$^2$, and even more.

Thus, the present invention provides a structure of the general type described in PCT/US93/06128, but in which the hydrogelling absorbent material is present in an amount which exceeds 120 g/m$^2$, and preferably exceeds 150 g/m$^2$ and more preferably exceeds 220 g/m$^2$.

Photomicrographic analysis of the product of the present invention shows that at least some of the bridges which connect the fibrous layers include along their length particles of the hydrogelling absorbent material linking at least two particles of the thermoplastic material.

It appears that it is by this means that relatively long bridges can be formed even with a high amount of the hydrogelling material being present.

It has been found that the amount of heat needed to achieve the desired structure is that which is sufficient to fuse the polymeric material in the core to a substantial extent, without affecting the cellulose fibres of the underlying fibrous layer.

In practice, that means that at least 50% of each of the polymeric particles becomes molten, and none of the cellulose fibres are yellowed.

It has been found that even when at least some of the particles of hydrogelling material are, in the dry state of the product, bonded to particles of thermoplastic material, when liquid is present the swelling of particles of hydrogelling material causes the links between those particles and those of the thermoplastic material to break, thus enabling the hydrogelling material to exhibit its full absorbent capacity.

Preferably the thermoplastic material makes up from 10% to 30% of the total weight of the mixture of hydrogelling absorbent material and thermoplastic material, more preferably from 15% to 20%.

It is desirable that the AGM used in the present invention should have a high absorption under pressure and a low gel permeability under pressure.

Preferably, the AGM used in the invention should have an absorption, under a pressure of 5 kPa, of at least 10 g/g, more preferably at least 12 g/g, still more preferably at least 15 g/g, and most preferably at least 17 g/g.

The AGM should moreover preferably have a gel permeability, under a pressure of 2 kPa, of not more than 150 sec, more preferably not more than 100 sec, and most preferably not more than 80 sec.

These characteristics assist in allowing the particles of AGM to swell when liquid is present, even if they are to a certain extent bonded to the thermoplastic material.

The following are some examples of AGM materials which can be used.

|  | Absorption under pressure (5 kPa) | Gel permeability under pressure (2 kPa) |
| --- | --- | --- |
| Drytech XZ 91002.01 (Dow Chemical) | 18.1 g/g | 60 sec |
| Favor SXM 300 (Chemische Fabrik Stockhausen) | 16.6 g/g | 141 sec |
| Aqualic L-76 (Nippon Shokubai) | 14.5 g/g | 131 sec |
| Aridall ASAP 2000 | 17.2 g/g | 60 sec |

| | Absorption under pressure (5 kPa) | Gel permeability under pressure (2 kPa) |
|---|---|---|
| (Chemdal) | | |

BRIEF DESCRIPTION OF THE DRAWINGS

Further characteristics and advantages of the invention will become clear from the description which follows, given purely by way of non-limiting example, with reference to the appended drawings in which:

FIG. 1 is a perspective view of a thin, layered, absorbent structure formed according to the present invention, with one of the two layers partially raised;

FIG. 2 is a sectional view of the thin, layered, absorbent structure, taken on the line II—II of FIG. 1;

FIG. 3 is a perspective view of a continuous strip of the thin, layered, absorbent structure of the present invention rolled in the form of a roll;

FIG. 4 is a plan view of a continuous strip of a alternative configuration of the thin, layered, absorbent structure;

FIG. 5 is a schematic view of a method for producing a thin, layered, absorbent structure according to the present invention;

FIG. 6 is a plan view of a disposable device for light or moderate incontinence using a thin, layered, absorbent structure according to the present invention as an absorbent element.

DETAILED DESCRIPTION OF THE INVENTION

Figure 7:
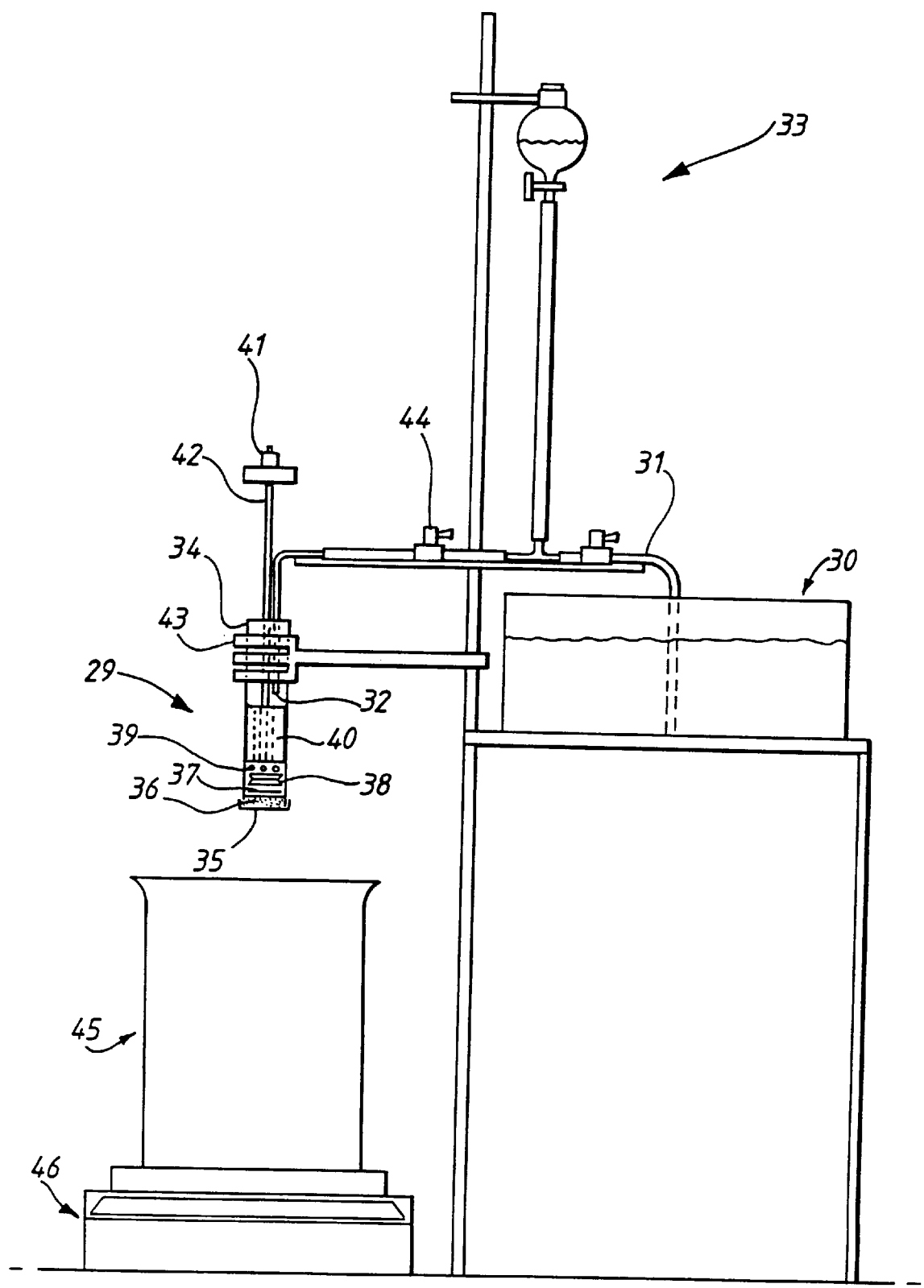
FIG. 7 is a diagram of an apparatus used to perform the gel permeability under pressure test described below.

The thin, layered, absorbent structures of the present invention will be described herein in relation to their use in disposable absorbent articles; the articles are worn by the user in direct contact with the body; their purpose is to absorb body fluids and they are then thrown away after a single use.

FIGS. 1 and 2 show a preferred configuration of a thin, layered, absorbent structure formed according to the present invention with one of the layers partially raised to show its construction more clearly.

In FIG. 1 it is possible to distinguish a first fibrous layer 1 and a second fibrous layer 2 in the form of two continuous strips of the same width, which are superposed so that their respective longitudinal edges 3 and 4 coincide; the fibrous layers may be made of various materials such as, for example, paper, wadding, or non-woven fabric; they are preferably made of dry-formed layers, generally referred to as "air laid" layers in English, of short cellulose fibres having a basic weight of between 20 g/m$^2$ and 150 g/m$^2$.

Alternatively, however, and more preferably, the second fibrous layer 2 may consist of a dry-formed mixture of cellulose fibres and bicomponent polyethylene/polypropylene fibres, such as, for example, those sold by Danaklon a/s of Varde, Denmark, as AL-Thermal E and AL-Thermal C.

Between the two fibrous layers 1 and 2 there is an intermediate layer 5 made of a mixture of particles of hydrogelling, absorbent material 6 and particles of a thermoplastic, polymeric, organic material 7; the width of the said intermediate layer 5 is less than that of the outer two fibrous layers 1 and 2 which extend beyond the intermediate layer 5 laterally forming two longitudinal edge portions 8 at their respective longitudinal edges 3 and 4.

The outer two fibrous layers 1 and 2 are bonded together in the central region in which the intermediate layer 5 is present by the application of heat and moderate pressure to melt the particles 7 of thermoplastic, polymeric, organic material present in the intermediate layer 5, mixed with the particles 6 of hydrogelling, absorbent material.

As can best be seen in FIG. 2, which is a section of the absorbent structure taken on the line II—II of FIG. 1, the bond between the fibrous layers 1 and 2 is generated by the melting of the individual particles 7 of thermoplastic polymeric, organic material; as it melts, the polymeric material forms "bridges" 9 comprising particles 6 of hydrogelling, absorbent material, which bridges connect the fibrous layers 1 and 2.

Moreover, the overall surface area of the bond points represents a small fraction of the surface area of the fibrous layers 1 and 2 and of the particles of hydrogelling, absorbent material, the absorption characteristics of which thus remain almost unchanged.

Two continuous lines 10 of adhesive are also applied to the two sides of the intermediate layer 5 on the longitudinal edge regions 8 of the two outer fibrous layers 1 and 2 so as to eliminate any further possibility of particles of hydrogelling, absorbent material 6 escaping from the longitudinal edges of the layered structure, which correspond to the superposed edges 3 and 4 of the two fibrous layers, and also reinforcing the connection between the fibrous layers themselves.

The hydrogelling material, which is preferably distributed in the form of particles 6, may be made of inorganic or organic substances such as cross-linked polymers, all known from the prior art.

The average dimensions of the particles 6, given as a weighted average of the smallest dimensions of the individual particles, may be between 100 microns and 800 microns.

The quantity of the hydrogelling absorbent material 6 in the intermediate layer 5 exceeds 120 g/m$^2$ and may, for example, be up to 600 g/m$^2$.

The finely-divided, thermoplastic, polymeric, organic material 7 has the purpose of bonding the two fibrous layers 1 and 2 together by melting and forming discrete, spaced-apart bond points 9 between the fibres of the two layers.

As explained above, the bridges which form these bond points involve particles of hydrogelling material as well as particles of thermoplastic, polymeric, organic material.

The quantity of thermoplastic, polymeric, organic material distributed and mixed with the hydrogelling, absorbent material is between 12 g/m$^2$ and 180 g/m$^2$.

The total of the hydrogelling, absorbent material and the thermoplastic, polymeric, organic material is thus in excess of 132 g/m$^2$, and may for example be up to 780 g/m$^2$.

The hydrogelling absorbent material preferably constitutes at least 77% of the total, and more preferably at least 83% of the total.

The thermoplastic, polymeric, organic material can preferably be melted at a temperature such as not to interfere with the characteristics of the other components of the layered structure, particularly the fibrous layers and the hydrogelling, absorbent material, though, as has now been found, the melting can be such as to bond the thermoplastic particles to the hydrogelling material.

Moreover, the thermoplastic material must have fluidity characteristics such as to enable the necessary bonds to be formed rapidly.

In the case of a thermoplastic material adjacent to either or both of the fibrous layers, when it melts, the individual particle is interpenetrated by fibres belonging to the fibrous layer and when it subsequently sets, it forms a bond point therewith.

It has been found that these preferred characteristics can be achieved by a thermoplastic, polymeric, organic material 7 having a melt flow index (M.F.I.), evaluated by the ASTM method D 1238-85 under conditions 190/2.16, of at least 25 g/10 min, preferably at least 40 g/10 min, and even more preferably at least 60 g/10 min.

If the layers 1 and 2 are made of a dry-formed short cellulose fibre material, it has been found particularly preferable to use a thermoplastic, polymeric, organic material composed of particles of high-density polyethylene with maximum dimensions of about 400 microns, characterised by a melt flow index of about 50 g/10 min, of which the quantity distributed is between 12 g/m$^2$ and 90 g/m$^2$.

It has been found that the apparent contradiction due to the incompatibility of polyethylene, which is typically hydrophobic, and, cellulose fibres is in fact translated into an advantage; in fact, it may be assumed that, during the heating of the structure, the melted polyethylene particle can rapidly incorporate the cellulose fibres belonging to the adjacent layer by virtue of the desired characteristics expressed in terms of the melt flow index, but does not interpenetrate the fibrous mass further, and thus creates a discrete and well-defined bond with the layer, and the effect of the polyethylene on the characteristics of the structure in terms, for example, of its absorption capacity, being limited to a maximum extent.

The thin, layered, absorbent structure of the present invention may also be formed from two different fibrous layers or may comprise more than two fibrous layers, and consequently more than one intermediate layer formed by the mixture of particles of hydrogelling, absorbent material and particles of thermoplastic, polymeric, organic material.

In any case, by virtue also of the continuous lines of adhesive disposed between the fibrous layers on the respective longitudinal edge portions which prevent the particulate material forming the intermediate layer from escaping from the longitudinal edges of the structure, the structure has the further advantage that it can be produced separately and stored as it is, for example, as a continuous strip rolled in the form of a roll 11, shown in FIG. 3, which can subsequently be used on the production line for disposable absorbent articles, for example, an absorbent article for light to moderate incontinence, which incorporate the structure as an absorbent element.

In an alternative configuration, shown in FIG. 4, the thin, layered, absorbent structure of the present invention comprises longitudinal edge portions 8' which are particularly wide and extend laterally beyond the continuous lines of adhesive 10; the thin, layered, absorbent structure can thus be shaped itself, for example, along cutting lines indicated 12, without involving the need to discard the material constituting the intermediate layer along with the scraps 13 formed from the superposed fibrous layers.

FIG. 5 is a simplified diagram of a method of producing a thin, layered, absorbent structure according to the present invention.

The reels 14, 15 supply the first and second fibrous layers 1 and 2, which may be of the same material or of different materials, in the form of respective continuous strips; the mixer/dispenser 16, which is supplied by the container 17 of hydrogelling, absorbent material and by the container 18 of thermoplastic, polymeric, organic material, forms the intermediate layer 5 on the surface of the first fibrous layer 1; the two extruders 19, only one of which is visible in FIG. 5, then form the two continuous lines 10 of adhesive, for example, of the hot melting type, at the two sides of the intermediate layer 5 and on the longitudinal edge portions of the first fibrous layer 1.

The first fibrous layer 1 and the intermediate layer 5 are heated to melt the particles of polymeric, organic material 7, for example, by means of a radiant heating element 20; the second fibrous layer 2 is then superposed on the first fibrous layer 1 and on the intermediate layer 5 and the three layers, combined to form the structure, are bonded by subjecting the structure to moderate pressure by passing it between the two rollers 21 and 22 bringing about the adhesion of the two fibrous layers 1 and 2 by means of the melted particles of polymeric, organic material 7, as explained above, and the two continuous lines of adhesive 10.

The outer surface of at least one of the two rollers 21 and 22 is preferably made resilient by being covered with a layer, for example, of silicone rubber.

Finally, the thin, layered, absorbent structure is collected on the reel 23 in the form of a continuous strip.

An incontinence device 24, shown in FIG. 6, which uses a thin, layered, absorbent structure formed according to the present invention, will be described by way of non-limiting example.

The absorbent device 24 is of the shaped type and is constituted by an upper liquid-permeable layer 25 made of a composite fibre/film coating structure of the type described in EP-A-0 207 904, partially perforated over a rectangular area of 60 mm in width extending longitudinally in the centre of the device, a secondary layer 26 formed by a 60 g/m$^2$ air-laid web of hydrophilic synthetic fibres produced according to Italian Patent Application No TO93 A 000 402, an absorbent element 27 formed by a thin, layered, absorbent structure according to the present invention, and a lower layer 28 which is impermeable to liquids, made from a coextruded polyethylene/polypropylene film 0.025 mm thick and 24.0 g/m$^2$ in weight.

The absorbent element 27, which is substantially rectangular, is 216 mm long and 56 mm wide with an overall thickness of 2 mm and a weight of 590 g/m$^2$.

The thin, layered absorbent structure constituting the absorbent element 27 comprises:

- an upper layer formed from thermal bonded air laid web of cellulose fibres and bicomponent polyethylene/polypropylene fibres 75 g/m$^2$;
- an intermediate layer formed from a mixture of 400 g/m$^2$ of particles of hydrogelling, absorbent material and 60 g/m$^2$ of particles of polyethylene;
- a lower layer formed from a resin-bonded air laid web of cellulose fibres 55 g/m$^2$.

The two continous lines of adhesive comprise two lines of hot-melt adhesive approximately 2 mm in width.

It will be seen that in this structure the hydrogelling material makes up about 70% by weight of the entire structure.

Naturally, the principle of the invention remaining the same, the details of construction may be varied widely from those described and illustrated without thereby departing from the scope of the present invention.

The following is an example of a layered, absorbent structure with five layers:

first fibrous layer formed from a 75 g/m² thermal bonded air laid web of cellulose fibres and bicomponent polyethylene/polypropylene fibres;

first intermediate layer formed from a mixture of 350 g/m² of particles of hydrogelling, absorbent material and 50 g/m² of particles of polyethylene;

second fibrous layer formed from a 55 g/m² resin bonded air laid web;

second intermediate layer identical to first intermediate layer;

third fibrous layer identical to second fibrous layer.

In the above description, the thermoplastic material has been referred to as being in the form of particles. It is to be understood that these "particles" need not necessarily be in the form of generally spherical bodies. They could for example, be in the form of fibrils.

These are very short fibres, and suitable fibrils include those available from Lextar V.O.F. of Rotterdam, Netherlands, under the trade mark PULPEX PE; these are polyethylene fibres having an average length of about 0.6–1.2 mm.

Methods used to measure various parameters mentioned above are described below.

ABSORPTION UNDER PRESSURE

Testing is performed using an apparatus known as a "demand wettability tester", illustrated in "Absorbency" edited by Pronoy K. Chatterjee and published by Elsevier Science Publishers B.V., 1985, page 62, with reference to B. M. Lichstein, "INDA Technical Symposium", USA, 1974, page 129.

The test is performed by placing a disk of non-woven hydrophilic material, 60 mm in diameter on the horizontal test sheet with the aperture in the centre.

A Plexiglas cylinder with an internal diameter of 50 mm is placed on the disk of non-woven material such that it too is centred over the aperture in the test sheet.

A quantity of 0.5 g of the AGM to be tested is then poured onto the non-woven disk inside the cylinder and pressure is exerted thereon by placing a 49 mm diameter Plexiglas piston on top of the hydrogelling, absorbent material and adding weights; weights are added until a total weight of 600 g is applied (equivalent to a pressure of 3 kPa), and further weights are then added until the total is 1000 g (equivalent to a pressure of 5 kPa).

Synthetic urine is then introduced through the aperture with a hydrostatic head of virtually zero and the hydrogelling, absorbent material is left to absorb the liquid for one hour.

The weight of the non-woven disk and of the hydrogelling, absorbent is measured, both before the test procedure is started and afterwards, and the difference noted to determine the weight of liquid $P_a$ absorbed by the AGM and non-woven disk combined.

The test is repeated for the non-woven disk alone to determine the amount of liquid $P_b$ absorbed by the disk itself.

The quantity of liquid absorbed by the hydrogelling, absorbent material, expressed in grams of liquid per gram of hydrogelling, absorbent material is calculated according to the equation:

Absorption under pressure $(g/g)=(P_a-P_b)/0.5$ where $P_a$: grams absorbed by the non-woven disk and by the hydrogelling, absorbent material $P_b$: grams absorbed by the non-woven disk only.

Two tests are performed for each type of hydrogelling, absorbent material and for the non-woven disk and the mean calculated.

GEL PERMEABILITY UNDER PRESSURE

The test is performed using the apparatus illustrated in FIG. 7 which shows a cylindrical container 29 for the superabsorbent and a syphon system comprising a large capacity tank 30 containing synthetic urine and a "U" tube 31 connecting the tank to the cylindrical container.

The "U" tube is positioned such that its open end 32 is 40 mm below the surface of the liquid in the tank.

The apparatus 33 comprising a separating funnel and stopcocks is required to eliminate air from the syphon circuit in a known manner before the test is begun.

The cylindrical cylinder 29 is made from a tube of Plexiglas 34 of a suitable length with an internal diameter of 30 mm; a layer 35 of 25 micron, 325 mesh nylon/ polyethylene fabric is stretched and fixed over the lower end of the tube 34.

The superabsorbent to be tested is selected by shaking it for 15 minutes in a "Fritsch Analysette 3" sieve so as to separate out the fraction with particle dimensions between 0.315 mm and 0.500 mm; the superabsorbent 36 selected in this manner is introduced into the cylindrical container 29 in a quantity of 0.226 g, such that it rests upon the fabric 35 closing the lower end of the tube.

150 ml of synthetic urine are placed in a 250 ml beaker, and the lower end of the cylindrical container is immersed three times in the liquid, before being reimmersed for a final time and left in the liquid for 30 minutes.

During this period, the following items are placed in the stated order on top of the superabsorbent 36 inside the cylindrical container 29: a disk 37 of 25 micron, 325 mesh nylon/polyethylene fabric of 30 mm in diameter, a perforated Plexiglas disc 38 of 29 mm in diameter and 7 mm in thickness provided with 20 radially arranged 2 mm apertures, 25 glass spheres 39 of 5 mm in diameter, a perforated cylindrical drum 40 of 28 mm in diameter and 30 mm in height provided with 8 apertures of 4 mm in diameter arranged in a circle, a weight 41 mounted on a rod 42 of a length such that it protrudes from the upper end of the cylindrical container 29; this combination being arranged such that a pressure of 2 kPa is exerted upon the superabsorbent 36.

The cylindrical container 29 is then raised and, keeping it constantly immersed in the beaker, attached to the pincers 43 as shown, such that the lower end 32 of the "U" tube 31 is located approximately 50 mm away from the upper surface of the layer of gel.

The stopcock 44 on the "U" tube is then opened, the 250 ml beaker is simultaneously removed and the synthetic urine is allowed to drip through the cylindrical container and the layer of gel into the 1000 ml beaker 45 placed underneath on the balance 46.

The first 50 g of synthetic urine are allowed to pass through or the level of liquid within the cylindrical container 29 is at least allowed to stabilise and then the time necessary for the next 50 g of synthetic urine to pass through is recorded.

Each type of superabsorbent is tested five times and the mean, standard deviation and percentage coefficient of variation are calculated CV %=[(standard deviation)/(mean)]×100

If the value of the percentage coefficient of variation is less than 10, the result is considered valid, if not a further five tests are performed.

COMPOSITION OF THE SYNTHETIC URINE USED IN THE TESTS

The synthetic urine is a solution of distilled water containing the following compounds (weight percent):

urea 2%, sodium chloride 0.9%, magnesium sulphate heptahydrate 0.11% calcium chloride dihydrate 0.06%.

What is claimed is:

1. A layered, absorbent structure, wherein the structure comprises, in combination, first and second layers (1, 2) of fibrous material and an intermediate layer (5) comprising a hydrogelling, absorbent material (3), in an amount exceeding 120 g/m², distributed between the first and second fibrous layers (1, 2), at least one of the first and second layers (1, 2) being permeable to liquids, and the intermediate layer (5) also comprising a thermoplastic, polymeric, organic material (7), the intermediate layer (5) bonding the first and second fibrous layers (1, 2) together, with the intermediate layer (5) between them.

2. An absorbent structure according to claim 1, wherein the first and second layers (1, 2) of fibrous material extend beyond the intermediate layer (5) laterally forming longitudinal edge portions (8), and in that the first and second layers (1, 2) of fibrous material are bonded together along each of the edge portions (8) by means of a continuous line of adhesive (10).

3. An absorbent structure according to claim 1, wherein the first and second layers (1, 2) of fibrous material have a basis weight of between about 20 g/m² and about 150 g/m².

4. An absorbent structure according to claim 1, wherein the quantity of the hydrogelling, absorbent material (6) distributed between the first and second fibrous layers (1, 2) is up to about 600 g/m².

5. An absorbent structure according to claim 1, wherein the quantity of thermoplastic material (7) present is between about 12 g/m² and about 180 g/m².

6. An absorbent structure according to claim 1, wherein the thermoplastic material (7) is present in the form of finely divided material.

7. An absorbent structure according to claim 1, wherein the thermoplastic material (7) has a melt flow index (M.F.I.) of at least 25 g/10 min.

8. An absorbent structure according to claim 1, wherein the absorbent structure is disposed in a disposable absorbent article between an upper liquid-permeable layer (25) and a lower layer (28) which is impermeable to liquids.

9. An absorbent structure according to claim 1, wherein the absorbent structure is disposed in an absorbent sanitary article made according to a method comprising the following steps:

providing a first continuous layer (25) of a liquid-permeable, flexible sheet material;

providing a second continuous layer (28) of a flexible sheet material which is impermeable to liquids;

providing at least one generally rectangular portion of the absorbent structure; and combining the first continuous layer (25), the second continuous layer (28) and the absorbent structure in a manner such that the absorbent structure is disposed and fixed between the first and second continuous layers (25, 28).

10. A layered, absorbent structure, wherein the structure comprises, in combination, first and second layers (1, 2) of a fibrous material with a basic weight of between about 20 g/m² and about 150 g/m², as well as an intermediate layer (5) comprising particles of a hydrogelling, absorbent material of which a quantity of from in excess of about 120 g/m² up to about 600 g/m² is distributed between the first and second fibrous layers (1, 2), at least one of the first and second fibrous layers (1, 2) being permeable to liquids, the first and second fibrous layers (1, 2) extending beyond the intermediate layer (5) laterally to form longitudinal edge portions (8), the intermediate layer (5) comprising a mixture of hydrogelling, absorbent material (6) and a quantity of between about 12 g/m² and about 180 g/m² of a finely divided thermoplastic, polymeric, organic material (7), which has a melt flow index (M.F.I.) of at least 25 g/10 min. and is intended to bond at least the first and second fibrous layers (1, 2) together with the intermediate layer (5) between them, forming discrete, spaced-apart bond spots (9), the layered, absorbent structure also being wherein the layers of fibrous material (1, 2) are bonded together along each longitudinal edge portion (8) by means of a continuous line of adhesive (10).

11. An absorbent structure according to claim 10, wherein the structure is generally rectangular.

12. An absorbent structure according to claim 10, wherein the structure comprises more than two layers of fibrous material with an intermediate layer (5) between each pair of fibrous layers, the intermediate layer comprising a mixture of hydrogelling, absorbent material (6) and finely divided, thermoplastic material (7).

13. An absorbent structure according to claim 10, wherein the layers of fibrous material (1, 2) comprise dry-formed layers of short cellulose fibres.

14. An absorbent structure according to claim 10, wherein the layers of fibrous material (1, 2) are made of different materials.

15. An absorbent structure according to claim 13, wherein one of the fibrous layers (1, 2) is made of a mixture of cellulose fibres and bicomponent polyethylene/polypropylene fibres.

16. An absorbent structure according to claim 10, wherein the thermoplastic material (7) has a melt flow index of at least 40 g/10 min, preferably at least 60 g/10 min.

17. An absorbent structure according to claim 10, wherein the thermoplastic material (7) is in the form of solid hot melting particles.

18. An absorbent structure according to claim 10, wherein the thermoplastic material is polyethylene-based.

19. An absorbent structure according to claim 18, wherein the thermoplastic material is in the form of a quantity of between about 12 g/m² and about 180 g/m² of polyethylene particles with maximum dimensions of 400 microns.

20. An absorbent structure according to claim 18, wherein the thermoplastic material (7) is in the form of fibrils.

21. An absorbent structure according to claim 10, wherein the adhesion lines (10) comprise a hot melting adhesive.

22. An absorbent structure according to claim 10, wherein the structure thickness is no more than 4 mm.

23. An absorbent structure according to claim 22, wherein its thickness is no more than 3 mm.

24. An absorbent structure according to claim 10, wherein the hydrogelling, absorbent material has an absorption under a pressure of 5 kPa of at least 10 g/g.

25. An absorbent structure according to claim 24, wherein the said absorption is at least 12 g/g.

26. An absorbent structure according to claim 25, wherein the said absorption is at least 15 g/g.

27. An absorbent structure according to claim 26, wherein the said absorption is at least 17 g/g.

28. An absorbent structure according to claim 10, wherein the hydrogelling, absorbent material has a gel permeability under a pressure of 2 kPa of not more than 150 seconds.

29. An absorbent structure according to claim 28, wherein the permeability is not more than 100 seconds.

30. An absorbent structure according to claim 29, wherein the permeability is not more than 80 seconds.

31. An absorbent structure according to claim 10, wherein the absorbent structure is made by a method comprising the following steps:

providing the first layer (1) of fibrous material;

providing the second layer (2) of fibrous material of a width such that it can contact the first layer (1) along respective longitudinal edge portions (8);

distributing a mixture of particles of hydrogelling, absorbent material (6), in an amount exceeding 120 g/m$^2$, as well as the finely divided, thermoplastic material (7) on the first layer (1) of fibrous material, the mixture being distributed in a manner such that the longitudinal edge portions (8) of the first layer (1) are left free;

applying lines of adhesive (10) to the longitudinal edge portions (8) of the first layer (1); and combining the first layer (1), the intermediate layer (5) and the second layer (2) in a layered structure by the application of heat and pressure to melt the thermoplastic material to a substantial extent, so as to form discrete, spaced-apart bond points (9) between the first layer (1) and the second layer (2), which have the intermediate layer (5) between them, with the lines of adhesive (10) bonding the first and second layers (1, 2) together along the longitudinal edge portions.

32. An absorbent structure according to claim 31 wherein the lines of adhesive (10) are applied in the form of continuous lines.

\* \* \* \* \*

UNITED STATES PATENT AND TRADEMARK OFFICE
CERTIFICATE OF CORRECTION

| | |
|---|---|
| PATENT NO. | : 5,944,706 |
| DATED | : August 31, 1999 |
| INVENTOR(S) | : Gianfranco Palumbo et al. |

It is certified that error appears in the above-identified patent and that said Letters Patent is hereby corrected as shown below:

Column 1,
Line 23, delete "retailing" and insert -- retaining --.

Signed and Sealed this

Seventh Day of February, 2006

JON W. DUDAS
*Director of the United States Patent and Trademark Office*